United States Patent [19]

Norén et al.

[11] Patent Number: 5,690,688
[45] Date of Patent: Nov. 25, 1997

[54] MEDICAL THERAPY APPARATUS WHICH ADMINISTERS THERAPY ADJUSTED TO FOLLOW NATURAL VARIABILITY OF THE PHYSIOLOGICAL FUNCTION BEING CONTROLLED

[75] Inventors: Kjell Norén, Solna; Jakub Hirschberg, Täby, both of Sweden

[73] Assignee: Pacesetter AB, Solna, Sweden

[21] Appl. No.: 745,735

[22] Filed: Nov. 12, 1996

[51] Int. Cl.$^6$ ................................ A61N 1/362
[52] U.S. Cl. .................................................. 607/17
[58] Field of Search ........................ 607/5, 6, 7, 9, 607/17

[56] References Cited

U.S. PATENT DOCUMENTS

| | | |
|---|---|---|
| 4,153,059 | 5/1979 | Fravel et al. ............ 607/41 |
| 4,732,157 | 3/1988 | Kaplan et al. |
| 5,265,617 | 11/1993 | Verrier et al. |
| 5,342,401 | 8/1994 | Spano et al. .............. 607/5 |
| 5,447,520 | 9/1995 | Spano et al. |

Primary Examiner—Scott Getzow
Attorney, Agent, or Firm—Hill, Steadman & Simpson

[57] ABSTRACT

In a medical therapy apparatus, such as a pacemaker, a physiological function which is to be artificially controlled by therapy administration has a natural variability associated therewith. The medical therapy apparatus generates a basic therapy which would otherwise be supplied to the subject in the absence of such natural variability. The medical therapy apparatus further includes a non-linear oscillator which emits a chaotic output, the chaotic output of the non-linear oscillator being matched to the variability of the physiological function in order to produce a variability adjustment. The basic therapy is combined with the variability adjustment and a variability-adjusted therapy is then administered to the subject.

30 Claims, 6 Drawing Sheets

MEDICAL THERAPY APPARATUS WHICH ADMINISTERS THERAPY ADJUSTED TO FOLLOW NATURAL VARIABILITY OF THE PHYSIOLOGICAL FUNCTION BEING CONTROLLED

BACKGROUND OF THE INVENTION

1. Field of the Invention

The present invention is directed to devices for administering medical therapy to a subject, and in particular to an implantable device which administers for therapy artificially controlling a physiological function which has a natural variability.

2. Description of the Prior Art

Many types of devices are known in the art for administering medical therapy to a subject. Many devices of this type are implantable, and many also obtain a measurement of the controlling physiological variable by a sensor which is also implanted, and which is connected in vivo to the therapy-administering device. Examples of implantable medical devices of this type are pacemakers, defibrillators, nerve enervators, infusion pumps, etc. In the case of pacemakers, for example, it is well-known to control the timing and/or energy content (amplitude) of pacing pulses dependent on one or more physiological variables, such as activity, blood oxygen content, respiration, cardiac impedance, etc. Each of these physiological measurements, or a selected combination thereof, is analyzed within the pacemaker, such as by identification of periodic events (waveforms) which occur in the measured physiological signals, in order to select a basic pacing rate. Once this basic pacing rate has been set, it will be used without variation until the occurrence of a subsequent "updating" routine, wherein the relevant measurement or measurements are repeated and again analyzed. The result of this update may indicate that the current basic rate is still suitable, and therefore no change in the basic pacing rate will be made. Alternatively, the current data may indicate that an adjustment of the pacing rate is needed, in which case an increase or decrease in the pacing rate and/or energy content of the pacing pulses will be set by the pacemaker control electronics.

Calculations made in conventional pacemaker electronics result in the emission of successive pacing pulses at precisely the same pulse-to-pulse interval, unless and until a change in the pacing rate is required. If, for example, as a result of the aforementioned physiological measurements and analysis, the pacemaker electronics determines that a basic pacing rate of 60 beats per minute (BPM) is warranted, the pulse generator of the pacemaker will be caused to emit a pacing pulse once each second, with exactly one second between the respective leading edges of successive pacing pulses. When examined closely, however, the natural behavior of the heart is not so precise. Even if, over time, a heart is determined to be beating at a nominal rate of 60 BPM, close investigation of the time between selected successive waveforms (for example R-waves) in the ECG reveals a natural, seemingly random, variability between such successive waveforms. Although on average the waveform-to-waveform period in the above example will be 1 second, when each individual period is analyzed, it may be found that a period lasting, for example, 0.98 seconds will be followed by a period lasting 1.01 seconds followed by a period lasting 1.0 seconds, followed by another period lasting 1.01 seconds, etc. The mathematical calculations and analysis which are undertaken in conventional pacemakers do not have any capability of introducing a randomness in the resulting calculation which matches or follows the natural variability of a heart.

Approaches have been proposed in the art, however, to quantify the beat-to-beat variability in physiologic waveforms, and to control the emission of pacing pulses based thereon. U.S. Pat. No. 4,732,157, for example, teaches sampling an ECG waveform at a number of fiducial locations for a number of beats, and to create a scatter plot for a given sample versus a number of preceding samples. A value is determined which minimizes the sum of the total distances of the points of the scatter plot in an equation, and the value of this parameter is assumed to be related to the electrical stability of the heart. The value of this parameter is then used as a predictor for a susceptibility to fibrillation.

Related U.S. Pat. Nos. 5,447,520 and 5,342,401 teach electrical stimuli are delivered to cardiac tissue at times which are determined using a chaos stabilizing algorithm. This algorithm utilizes a real time calculation based on a system parameter which is experimentally determined by the electrical stimuli.

For diagnostic purposes, U.S. Pat. No. 5,265,617 discloses a method and apparatus for non-invasively tracking and diagnosing cardiac vulnerability to ventricular defibrillation by identifying T-wave alternation and head rate variability, and these phenomena are simultaneously analyzed and used to assess the extent and cause of cardiac vulnerability to ventricular fibrillation.

Primarily beginning with investigations by Mandelbrodt, analysis of so-called chaotic behavior has evolved into the field known simply as "chaos." A so-called chaotic system is, in reality, deterministic in the sense that predictions as to the future behavior of the system can be made based on one or more fixed rules. Although the system may have an appearance of being random, this is usually because the system has not been observed for a sufficiently long time. In a true random system, the "randomness" of its behavior does not decrease when the observation time is increased. By contrast, the output of a chaotic system is, in principle, fully determined from its past history. In practice, however, many such system have variables which are exponentially sensitive to or dependent on the initial conditions at a given point in time, thereby making predictions about future behavior of the system extremely complicated, so that despite knowing the "rules" the systems are still unpredictable.

For systems which do not exhibit the exponential sensitivity which precludes their rational analysis, a number of "standard" systems have been analyzed in the literature. The ability to predict the future behavior of a chaotic system depends, in pad, on the identification of one or more attractors possessed by the system. Various types of standard systems are known which respectively have different numbers of attractors, and wherein the attractors behave or interrelate in different manners. For a given system under analysis, a common approach is to analyze the number of attractors in this system, and to mathematically define their interrelation, so that the system in question can be matched to the standard system which it most closely resembles. A number of such known chaotic systems in the literature are the Lorentz system, the Duffin system, the Rössler system, and the Mackey-Glass system. Detailed descriptions and mathematical representations and models of these systems can be found in any standard text in the literature relating to chaotic systems.

SUMMARY OF THE INVENTION

It is an object of the present invention to provide a medical therapy apparatus which artificially controls a physiological function having a natural variability, wherein the therapy administered for controlling the physiological function is matched to the natural variability of the physiological function.

The above object is achieved in accordance with the principles of the present invention in a medical therapy apparatus having means for generating a basic therapy for artificially controlling a physiological function of a subject, the physiological function having a natural variability associated therewith, a non-linear oscillator, means for matching the output of the non-linear oscillator to the natural variability of the physiological function to provide a variability adjustment, means for combining the basic therapy and the variability adjustment to generate a variability-adjusted therapy, and means for administering the variability-adjusted therapy to the subject.

The medical therapy apparatus may, for example, be a pacemaker, in which case the basic therapy will be a series of pacing pulses and the variability adjustment will be for the purpose of adjusting the timing between successive pulses in order to match the overall series of pacing pulses to the natural variability of the heartbeat rate of the subject.

In an embodiment wherein the medical therapy apparatus is a pacemaker, one or more physiological measurements can be obtained from the subject, and the basic therapy can then be generated dependent on one of these measurements or a combination of these measurements.

The non-linear oscillator can be constructed and operated so as to replicate any known, well understood chaotic system, such as the aforementioned Lorentz system, Duffin system, Rössler system or Mackey-Glass system.

DESCRIPTION OF THE PREFERRED EMBODIMENTS

Figure 1:
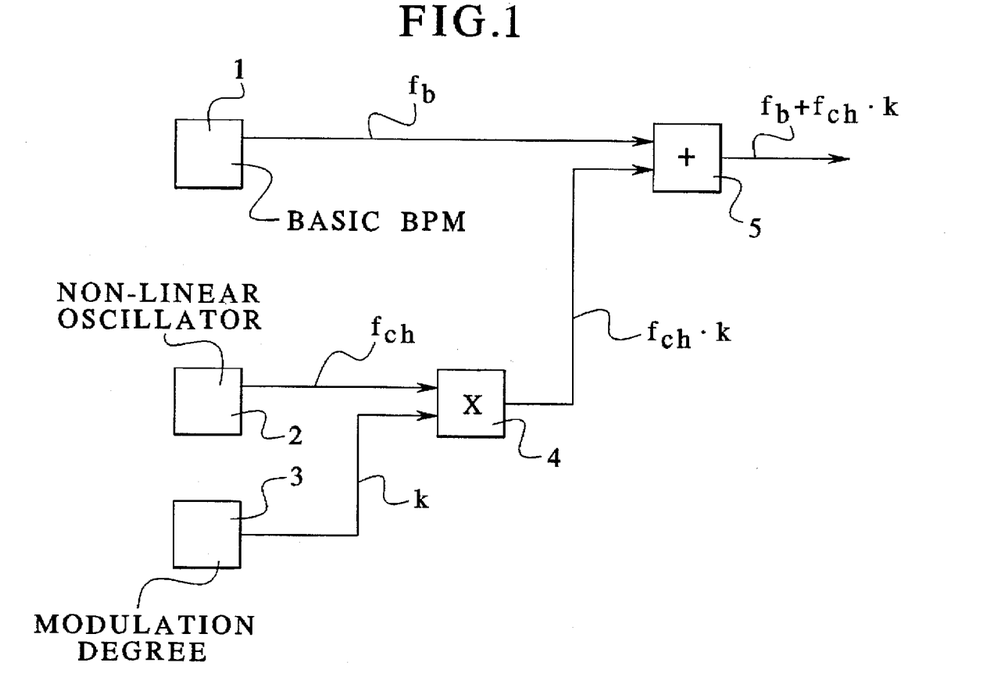
FIG. 1 is a schematic block diagram for explaining the basic concept of the invention.

FIG. 1 is a schematic block diagram which illustrates the basic principles underlying the present invention. The block diagram illustrates an example wherein a set value (basic therapy) for a pacemaker stimulation rate is modulated a few beats per minute by a chaotic oscillator. A set value $f_b$ is emitted by a basic BPM unit 1. A non-linear (chaotic) oscillator 2 emits an output $f_{ch}$. This output is multiplied by a modulation degree (scaling factor) k, emitted by a modulation degree unit 3. The multiplication takes place in a multiplier 4, to produce a product $f_{ch} \cdot k$. This product is added in an adder 5 to the set value $f_b$, to produce the sum $f_b + f_{ch} \cdot k$. This sum is then used to control the emission of stimulation pulses in a pacemaker, as described in more detail below. In this context, the product $f_{ch} \cdot k$ constitutes a variability adjustment, and the therapy administered dependent on the sum $f_b + f_{ch} \cdot k$ constitutes variability-adjusted therapy.

The modulation degree or scaling factor k can be set at a constant value, or can be varied in a programmable or calculatable manner. The value of the modulation degree k determines the degree of modulation of the set value by the output of the non-linear oscillator 2. If the modulation degree is set to zero there will be no modulation at all.

The set value can be the conventional rate set by known techniques in a pacemaker system, for example, the heartbeat rate measured in an activity-controlled pacemaker. As described in the embodiment discussed in detail below, it is an advantage if this rate, which be averaged over a floating time window, can be used to influence the modulation degree. This advantage can be achieved by using a fraction of the set value to control the value of the modulation degree k emitted by the modulation degree unit 3. Alternatively, the modulation degree k can be a constant value, and multiplication by the aforementioned fraction can take place in a separate multiplication stage, downstream from the modulation degree unit 3. Adjusting the modulation degree dependent on the set rate allows different rate modulations at different heartbeat rates.

Figure 2:
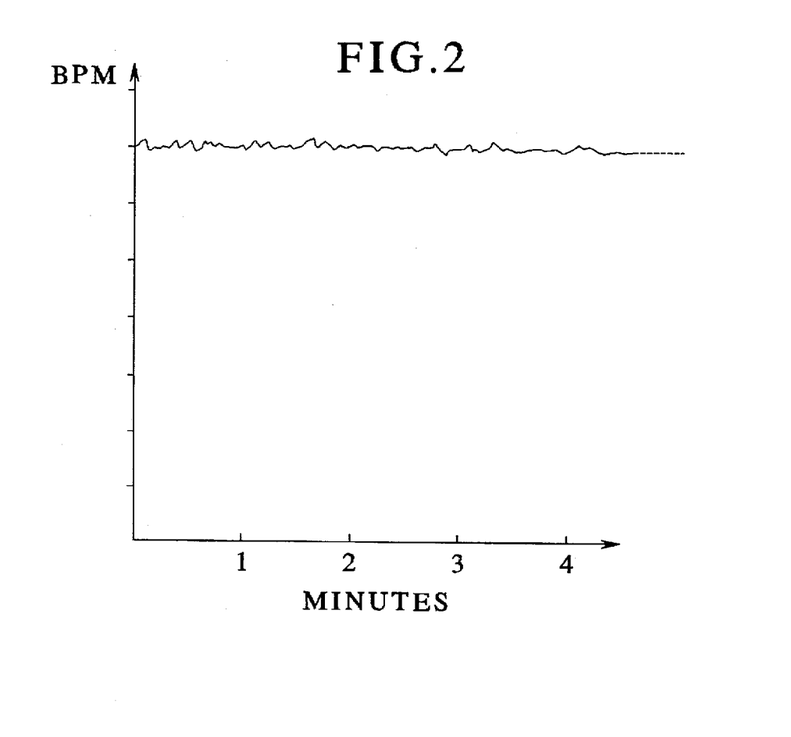
FIG. 2 is a graph showing heartbeats per minute (BPM) versus time (measured in minutes) for illustrating the natural variability of the heartbeat rate.

FIG. 2 shows the variability-adjusted BPM which arise using the exemplary arrangement of FIG. 1 with $f_b=70$ and k=0.25. As can be seen, although the beats per minute is consistently at or near the basic value of 70, the time between successive beats will not be precisely 1 min./70, but will chaotically change relative to that basic value.

Figure 3:
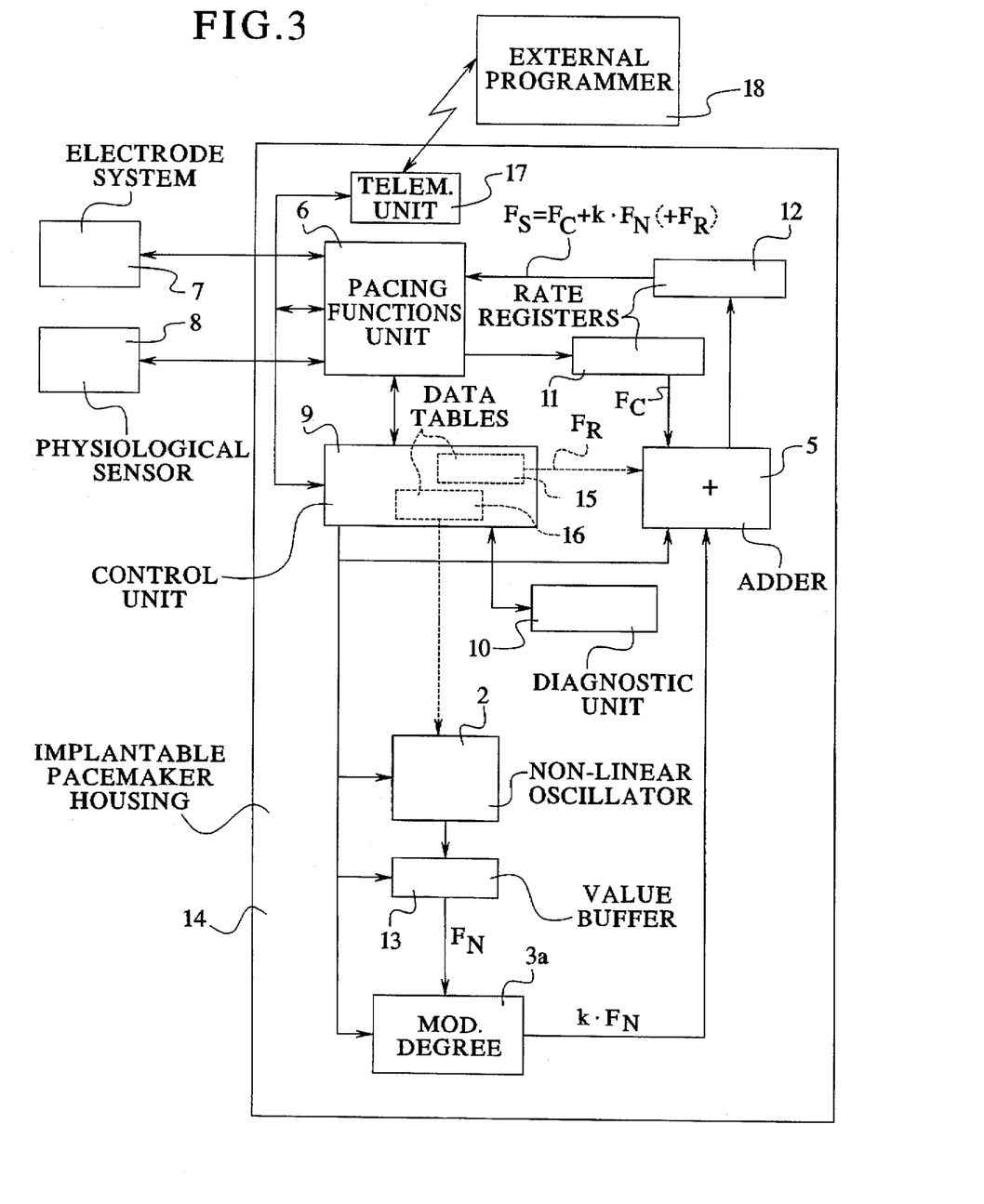
FIG. 3 is a block diagram of an implantable pacemaker constructed and operating in accordance with the principles of the present invention.

An exemplary embodiment of a pacemaker operating in accordance with the principles of the present invention is shown in FIG. 3. This system employs a pacing functions unit 6, which includes a pulse generator of any suitable type. The pacing functions unit 6 emits pacing pulses which are delivered to a subject via an electrode system 7, electrically connected to the pacing functions unit 6 in a known manner. The pacing functions unit 6 may also be electrically connected to a physiological sensor 8 (as well as to additional physiological sensors, not shown) for receiving different types of physiological measurements from the subject. The pacing pulses emitted by the pacing functions unit 6 and delivered via the electrode system 7 are intended to artificially control the heartbeat rate of the subject.

The pacing functions unit 6 is supplied with control signals from a control unit 9. The control unit 9 is also in communication with a diagnostic unit 10, which can actively conduct diagnostics for checking the pacemaker operation, and can also store data for periodic interrogation by or dumping data to an external programmer 18. The external programmer 18 is in communication with the implanted unit via a telemetry unit 17. The telemetry unit 17 is in two-way communication with the control unit 9 for receiving data therefrom (as well as data from the diagnostic unit 10) and for supplying data and programming instructions thereto.

The control unit 9 also supplies control signals to the non-linear oscillator 2. The non-linear oscillator 2 has an output connected to a value buffer 13, which is also controlled by the control unit 9. The output of the value buffer is a chaotic component $F_n$, which is supplied to a modulation degree unit 3a. The modulation degree unit 3a in the embodiment of FIG. 3 is a combination of the modulation degree unit 3 and the multiplier 4 in the example of FIG. 1, and thus emits an output which is a product $k \cdot F_N$. The modulation degree unit 3a is also controlled by the control unit 9.

The output of the modulation degree unit 3a is supplied to the adder 5. Another input to the adder 5 is supplied with a conventional pacing rate $F_c$. This conventional pacing rate is determined by any suitable conventional manner. In the embodiment of FIG. 3, the measurement from the physiological sensor 8 is evaluated within the pacing functions unit 6. The result of this evaluation is supplied to a rate register 11, wherein a number of different pacing rates are stored, correlated with different evaluation results, such as in a look-up table. Dependent on the evaluation result supplied thereto by the pacing functions unit 6, the rate register 11 emits an appropriate conventional pacing rate $F_C$.

The sum produced by the adder 5 is supplied to a further rate register 12. The aforementioned rate register 11 contains conventional rates at which the pacemaker would operate without the presence of the non-linear oscillator 2. The further rate register 12 stores a number of different pacing rates which control the actual stimulation rate of the pacemaker shown in the embodiment of FIG. 3, i.e., the rate register 12 emits a variability-adjusted stimulation rate which takes into account the natural variability of the heart, as modeled by the non-linear oscillator 2. If k=0 the rate register 12 would select (emit) the same rate $F_c$ as the rate register 11. The actual stimulation rate $F_s$ emitted by the rate register 12 is, as described in connection with FIG. 1, a combination of the conventional rate and the product of the chaotic rate $F_n$ multiplied by the modulation degree k. This value is supplied to the pacing functions unit 6, which emits pacing pulses at the variability-adjusted rate $F_S$, which are delivered to the subject via the electrode system 7.

It is also possible to add a random component $F_R$ in the calculation leading to the variability-adjusted stimulation rate $F_S$. This option is indicated by the generation of such a random component $F_R$ in a data table 15 contained in the control unit 9. Alternatively, the random component $F_R$ can be generated by another non-linear oscillator. If the random component $F_R$ is used, it is supplied to the adder 5 together with the product $k \cdot F_N$ and $F_C$, and is added to those values in the adder 5. This results in the random component $F_R$ being present as a further addend in the expression for the variability-adjusted stimulation $F_S$. The optional presence of $F_R$ in that expression is indicated by its inclusion within dashed line parentheses.

Another option is to initialize the data in the non-linear oscillator 2. It is known that some chaotic systems operate without any external data input, and these are known as autonomous oscillators or autonomous systems. By contrast, a non-autonomous system requires an external data feed. In addition to initializing the data in a non-linear oscillator 2, if the non-linear oscillator 2 is used to model a non-autonomous system, the data feed from the control unit 9 can also serve as the necessary external data feed. This option is indicated by a further data table 16 in the control unit 9.

The output $F_N$ of the value buffer 13 is preferably in digital form, and therefore the value buffer 13 can include an analog-to-digital converter if the active portion of the non-linear oscillator 2 produces an analog output. Alternatively, a separate analog-to-digital converter can be inserted between the value buffer 13 and the modulation degree unit 3a.

Figure 4:
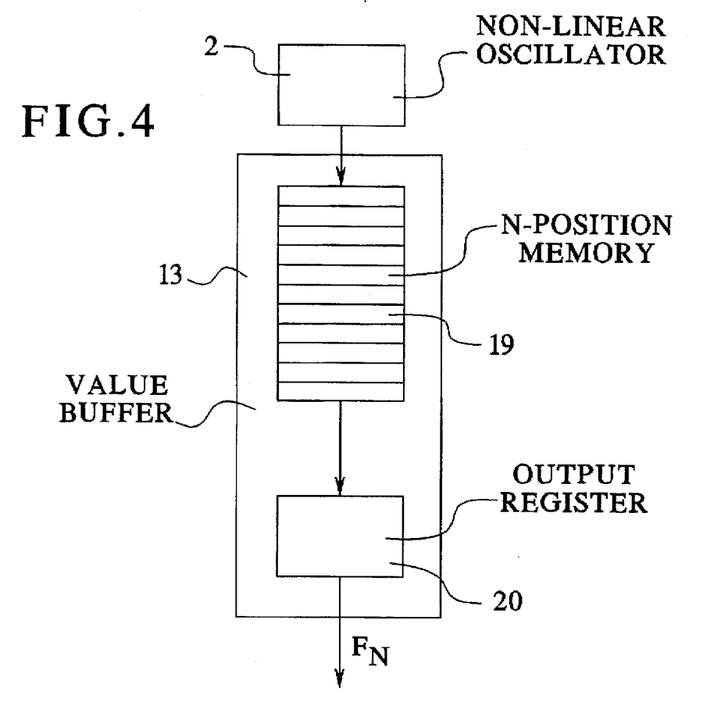
FIG. 4 is a block diagram showing a first embodiment for the value buffer for use in the embodiment of FIG. 3.

As shown in FIG. 4, one embodiment for the value buffer 13 includes an N-position memory 19 and an output register 20.

This embodiment assumes that the input to the N-position memory 19 will be in digital form, and thus if the output of the non-linear oscillator 2 is in analog form, an analog-to-digital converter will be included between the output of the non-linear oscillator 2 and the input of the N-position memory 19. The output of the non-linear oscillator 2, either in its original digital form or after conversion, will typically contain four to eight bits of information. Each memory location of the N-position memory 19 stores one output sample from the non-linear oscillator 2. The N-position memory 19 can be organized a FIFO (first in, first out) memory. The N-position memory 19 is operated by the aforementioned control signal from the control unit 9 which includes address, read and write controls.

The arrangement in FIG. 4 allows different time scales for data read-in and data read-out. For example, time "stretching" can be accomplished by rapid read-in and slow read-out of the memory 19. For example, 1000 values can be obtained from the non-linear oscillator 2 and stored at a rapid speed, with one value then being read out for each stimulation (pacing) interval. If desired, the last internal states of the non-linear oscillator 2 can be saved in a state memory (not shown) and then used to re-initialize the non-linear oscillator 2, instead of obtaining initialization data from the data table 16.

Moreover, it is not necessary to store every value from the non-linear oscillator 2 in the memory 19. It is possible to achieve the goal of generating an output $F_N$ which provides for adjustment of the natural variability by obtaining the standard deviation for a few beats over a time period of, for example, one minute. This is most apparent when the underlying mechanism for the non-linear oscillator 2 is a system of differential equations, such as when the non-linear oscillator 2 models a Mackey-Glass system. It is, of course, not possible to take samples at infinitely short time intervals, since this would result in an infinite range of values with infinitely small variations. Thus, one must make a compromise among the type of system modeled by the non-linear oscillator 2, the internal time steps within the non-linear oscillator 2, the selection of the output samples, and the desired variability which is intended to be represented by $F_N$.

It should be noted that the output values from the non-linear oscillator 2, by their very nature, will not be periodic, and therefore sampling the output of the non-linear oscillator 2 equidistant points in times will not create a periodic result.

Figure 5:
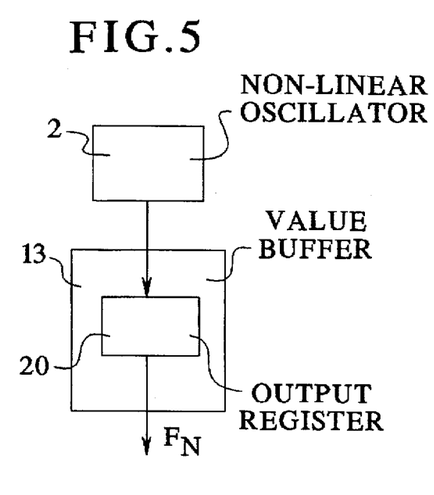
FIG. 5 is block diagram of a second embodiment for the value buffer for use in the pacemaker of FIG. 3.

The output register 20 may be a part of the memory 19, however, it is also possible to operate without the memory 19 at all, in which case the output of the non-linear oscillator 2 (after analog-to-digital conversion, if necessary) is supplied directly to the output register 20, as shown in FIG. 5. In this embodiment, the value buffer merely includes the output register itself. This embodiment can be used when the output of the non-linear oscillator 2 is digital, i.e., the result of solving a finite differential equation by software or digital hardware. In this embodiment, the next step in the iteration of the non-linear oscillator 2 is initiated by a new stimulation interval, i.e., each new interval produces the next value from the non-linear oscillator 2.

It is also possible to employ combinations of the embodiments shown in FIGS. 4 and 5, for example, to save a range of values from the output of a digital non-linear oscillator 2 in a memory, and then to simply fetch these values as needed, without the time compression or expansion achieved by dynamic control of the memory 19 in the embodiment of FIG. 4. Another, less practical possibility, if the output of the non-linear oscillator 2 is in analog form, is to employ a sample and hold circuit which obtains one sample of the output of the non-linear oscillator 2 within each stimulation interval, and holds that value until a next stimulation interval.

Figure 6:
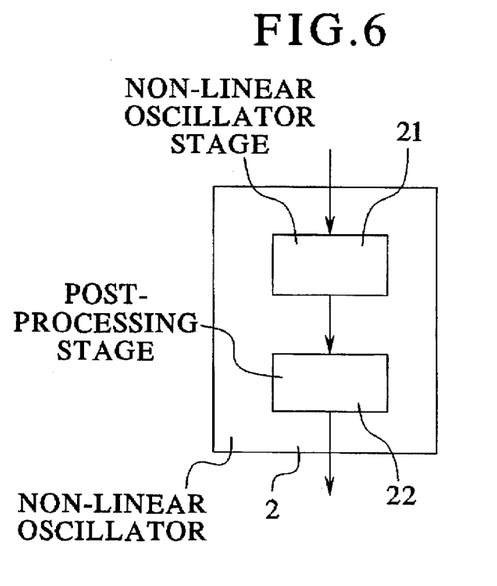
FIG. 6 is a block diagram for the non-linear oscillator for use in the pacemaker of FIG. 3.

The non-linear oscillator 2, as shown in FIG. 6, may include a non-linear oscillator stage 21 having an output connected to a post-processing stage 22, with the output of the post-processing stage 22 forming the output of the non-linear oscillator 2. This embodiment has utility when the non-linear oscillator stage 21 is a "pure" oscillator, for example a Lorentz type oscillator. In such a situation, the post-processing stage 22 can add a simple function, such as scaling or subtraction of a baseline, in order to make the average of the post-processing stage 22 equal to zero (i.e., the output of the post-processing stage 22 still exhibits non-zero values, but when averaged, these non-zero values produce an average of zero).

Non-linear operation is also possible within the post-processing stage 22, for example a floating median value of the output of the non-linear oscillator stage 21 can be calculated over a number of samples of the output of the non-linear oscillator stage 21, for example, five samples.

It is also possible to undertake the post-processing after the value buffer 13.

All of the above components except the electrode system 7, the physiological sensor 8 and the external programmer 18 are contained in a pacemaker housing 14 of a size and shape suitable for implantation in a subject.

Examples of how the output of the non-linear oscillator 2 is used are shown in FIGS. 7a and 7b, 8a and 8b, 9a and 9b, and 10a and 10b respectively using different numbers of samples (i.e., different time steps). In each of these examples, the output of the non-linear oscillator 2 is the Z-component of a Lorentz system, with the nominal output value being processed so that the average level is zero, and the amplitude is at a 15% level. The original values were calculated rapidly, and stored in a memory.

Figure 7A:
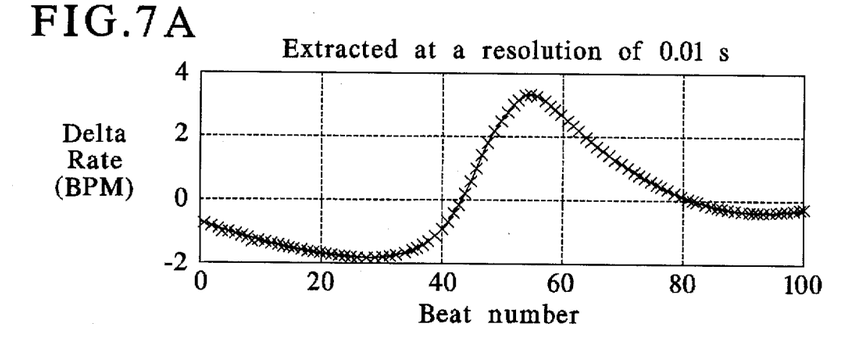
FIGS. 7a and 7b illustrate the influence of the non-linear oscillator in the pacemaker of FIG. 3 on the stimulation rate, with a resolution of 0.01s.
Figure 7B:
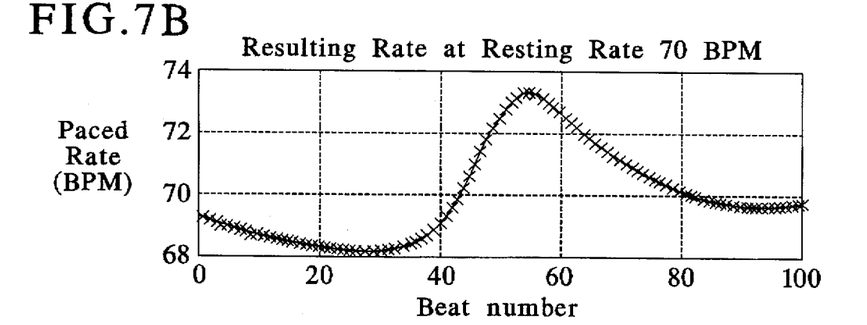

FIGS. 7a and 7b show a time step of 0.01s. This means that the "sampling frequency" is 100 Hz, although this may not be the actual frequency in real time.

By selecting all of the samples, or using a pre-selected set of the samples, it is possible to control the shape of the variability curve over time. In each of the examples, the average paste rate is 70 BPM, with a substantially constant standard deviation calculated over a time interval of 100 beats (1 minute and 26 seconds). As can be seen, the change in the curve shape is from a very smooth rate change to a larger change from beat to beat. The resting rate in each example is the basic programmed rate in the pacemaker. In each example, $F_C$ is a constant 70 BPM, with k·$F_N$ being shown in the upper graph of each example, and $F_R$0. The resulting $F_S$ is shown in the lower plot in each example.

Figure 8A:
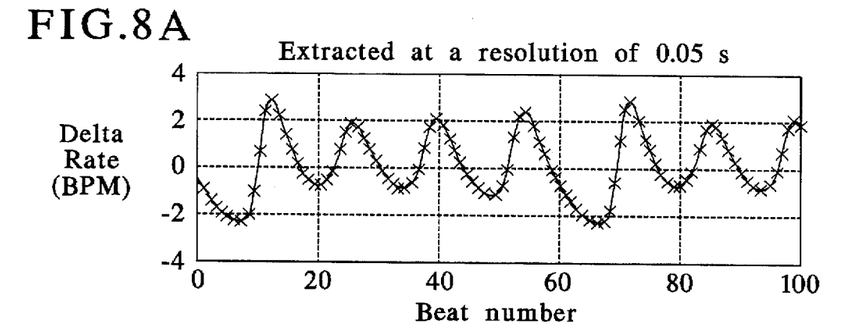
FIGS. 8a and 8b illustrate the influence of the non-linear oscillator in the pacemaker of FIG. 3 on the stimulation rate, with a resolution of 0.05s.
Figure 8B:
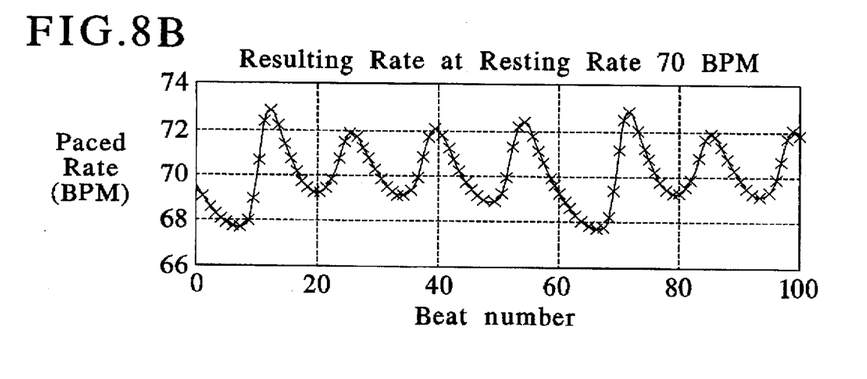
Figure 9A:
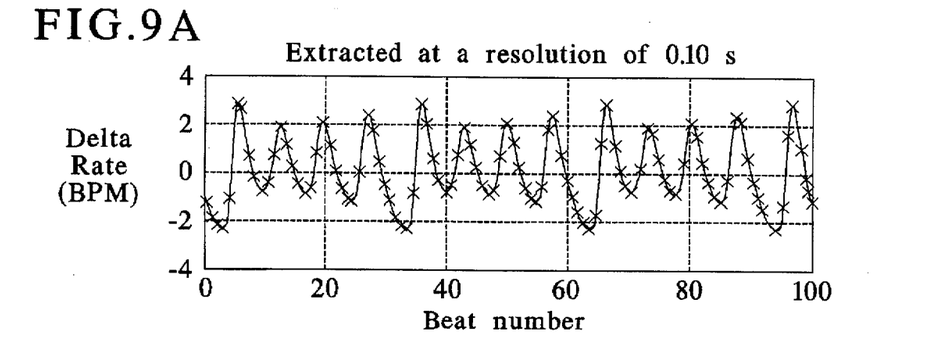
FIGS. 9a and 9b illustrate the influence of the non-linear oscillator in the pacemaker of FIG. 3 on the stimulation rate, with a resolution of 0.10s.
Figure 9B:
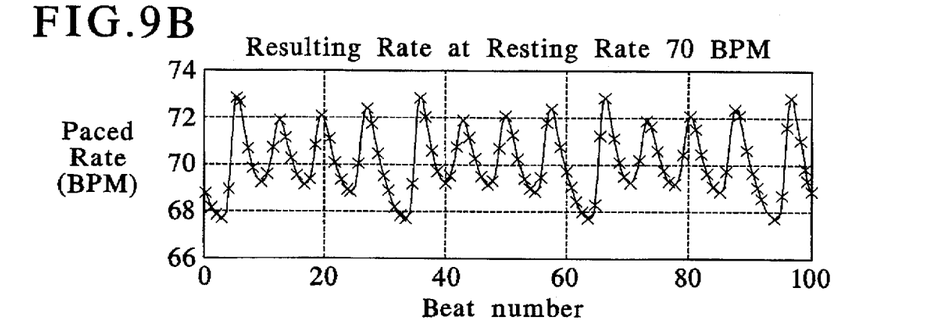
Figure 10A:
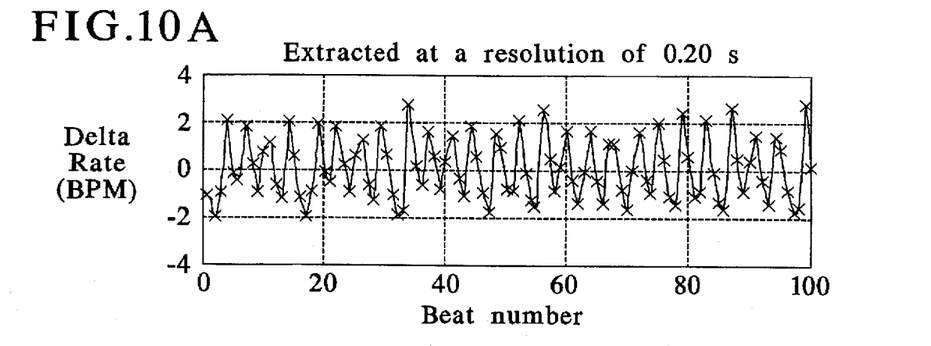
FIGS. 10a and 10b illustrate the influence of the non-linear oscillator in the pacemaker of FIG. 3 on the stimulation rate, with a resolution of 0.20s.
Figure 10B:
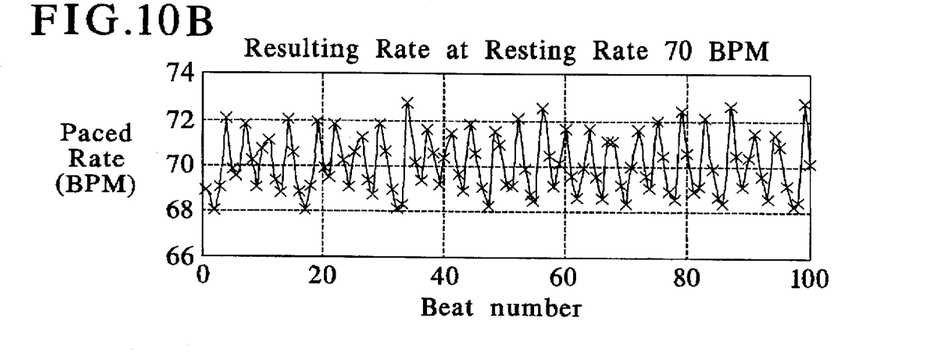

FIGS. 8a and 8b show the result with a resolution of 0.05s, FIGS. 9a and 9b show the result with a resolution of 0.10s, and FIGS. 10a and 10b show the result with a resolution of 0.20s.

Figure 11:
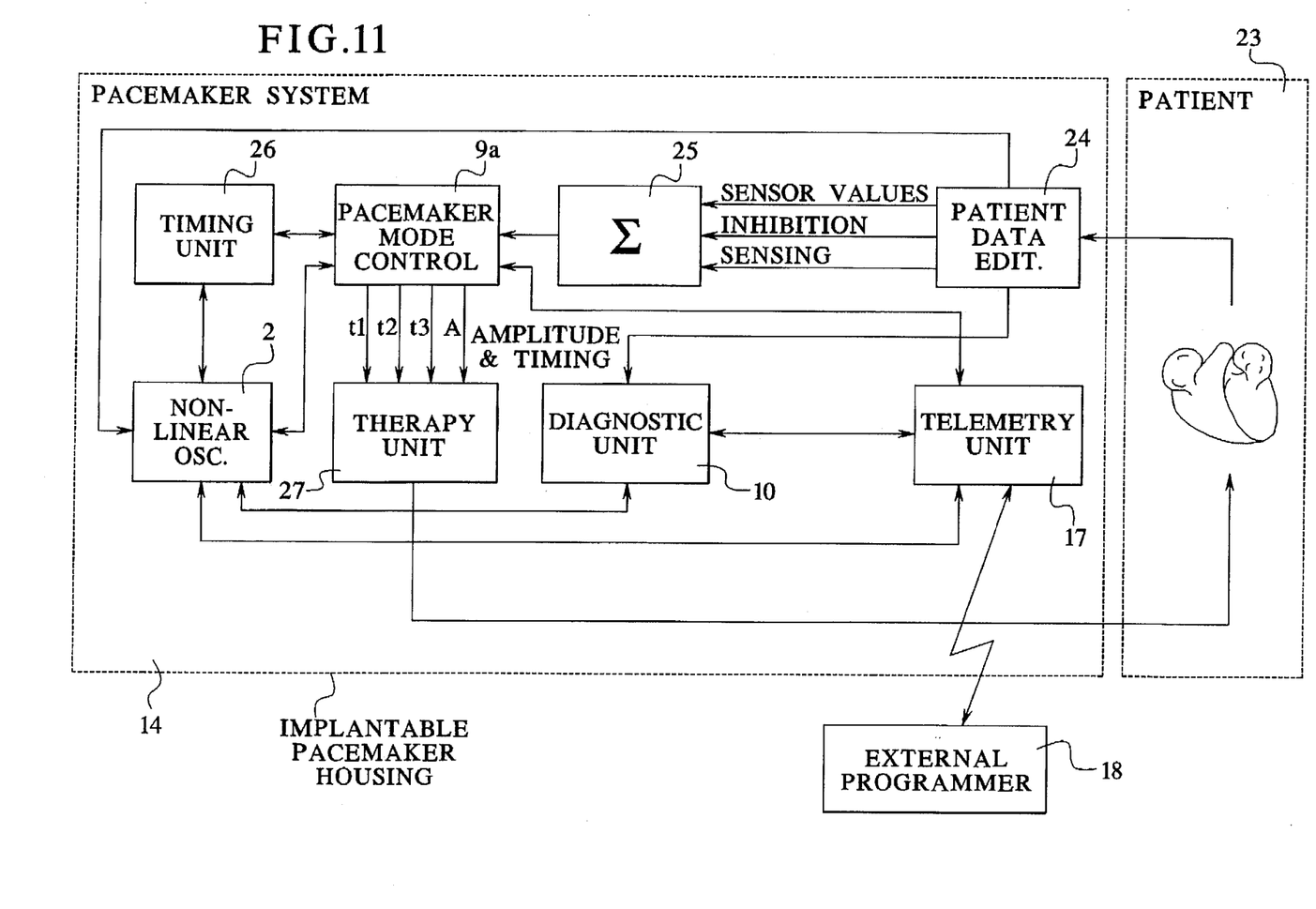
FIG. 11 is a block diagram showing a pacemaker system employing a non-linear oscillator as a random variable generator for producing variables for a number of test procedures.

It is also possible to use the non-linear oscillator 2 as a random data source in the operation of a pacemaker. An example of such a pacemaker is shown in FIG. 11. A random data source is needed in certain types of control techniques, including programming, testing and load investigation procedures. In the embodiment of FIG. 11, components already identified in connection with the embodiment of FIG. 3 have been provided with the same reference numerals, and need not be described again. The pacemaker system shown in FIG. 11 interacts in vivo with a schematically-indicated patient 23, via leads and sensors of the type shown in more detail in FIG. 3. Patient data editing stage 24, which may also temporarily store incoming data. From the raw, incoming data, the patient data editing unit 24 generates, in a known manner, sensor values, inhibition signals and sensing signals, as needed. These signals are combined in a summing unit 25 in a known manner and are supplied to a pacemaker mode control unit 9a. The pacemaker mode control unit is programmed to select one of several available therapy (pacing) modes and emits timing information t1, t2 or t3 corresponding to the selected modes. Once the therapy mode has been selected, the pacemaker mode control unit 9a also controls the amplitude of the emitted pulses, by means of a signal A.

The selected mode and the amplitude and timing signal A are supplied to a therapy unit 27, which interacts with the patient 23 in a known manner to deliver the selected therapy.

The pacemaker mode control unit 9a is connected to a conventional timing unit 26.

The pacemaker mode control unit 9a and the timing unit 26 are also both connected to the non-linear oscillator 2. The non-linear oscillator 2 is also supplied with edited patient data from the patient data editing unit 24. The non-linear oscillator 2 is also in communication with the diagnostic unit 10 and the telemetry unit 17 for assisting in programming and testing procedures.

As noted above, many types of modern programming operate on a so-called "multi-parameter" basis, which have the capability of permitting a large number of different simulated situations and models to be set up and tested. In order to run through the large number of test situations with different variables, the non-linear oscillator 2 is used to produce random variables for such testing. The simulated results of all of these different test situations can then be analyzed and the best or optimum result can be selected for use in controlling the pacemaker.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical therapy apparatus comprising:

means for generating a basic therapy for artificially controlling a physiological function of a subject, said physiological function having a natural variability associated therewith;

a non-linear oscillator having an output;

means for matching said output of said non-linear oscillator to said natural variability of said physiological function to produce a variability adjustment;

means for combining said basic therapy and said variability adjustment to generate a variability-adjusted therapy; and means for administering said variability-adjusted therapy to said subject.

2. A medical therapy apparatus as claimed in claim 1 further comprising:

means for obtaining a physiological measurement over time from said subject; and said means for artificially controlling a physiological function of said subject comprising means for artificially controlling said physiological function of said subject dependent on said physiological measurement.

3. A medical therapy apparatus as claimed in claim 1 wherein said means for matching said output of said non-linear oscillator to said natural variability of said physiological function comprises means for multiplying said output of said non-linear oscillator by a scaling factor.

4. A medical therapy apparatus as claimed in claim 3 wherein said basic therapy has a basic therapy value associated therewith, and further comprising means for setting said scaling factor as a fraction of said basic therapy value.

5. A medical therapy apparatus as claimed in claim 1 wherein said non-linear oscillator comprises means for modeling a chaotic system.

6. A medical therapy apparatus as claimed in claim 1 wherein said non-linear oscillator comprises means for modeling a Lorentz system.

7. A medical therapy apparatus as claimed in claim 1 wherein said non-linear oscillator comprises means for modeling a Duffin system.

8. A medical therapy apparatus as claimed in claim 1 wherein said non-linear oscillator comprises means for modeling a Rössler system.

9. A medical therapy apparatus as claimed in claim 1 wherein said non-linear oscillator comprises means for modeling a Mackey-Glass system.

10. A medical therapy apparatus as claimed in claim 1 further comprising means for generating a random value from said basic therapy and wherein said means for combining comprises means for combining said basic therapy, said variability adjustment and said random value to generate said variability-adjusted therapy.

11. A medical therapy apparatus as claimed in claim 1 further comprising means for initializing said non-linear oscillator with initial data values.

12. A medical therapy apparatus as claimed in claim 1 wherein said non-linear oscillator comprises means for modeling an autonomous chaotic system.

13. A medical therapy apparatus as claimed in claim 1 wherein said non-linear oscillator comprises means for modeling a non-autonomous chaotic system and further comprising means for supplying said means for modeling a non-autonomous chaotic system with an external data feed.

14. A pacemaker for artificially controlling a heartbeat rate of a subject, said heartbeat rate having a natural variability associated therewith, said pacemaker comprising:

pulse generator means for generating a plurality of successive pacing pulses respectively separated by pulse intervals;

control means for setting a basic pacing rate;

a non-linear oscillator having an output;

means for matching said output of said non-linear oscillator to said natural variability of said heartbeat rate to produce a variability adjustment;

means for combining said basic rate with said variability adjustment to generate a variability-adjusted stimulation rate, said pulse generator means emitting said stimulation pulses at said variability-adjusted stimulation rate; and means for delivering said stimulation pulses at said variability-adjusted stimulation rate to a heart of said subject.

15. A pacemaker as claimed in claim 14 further comprising:

means for obtaining a physiological measurement over time from said subject; and said control means for artificially controlling a physiological function of said subject comprising means setting said basic pacing rate dependent on said physiological measurement.

16. A pacemaker as claimed in claim 14 wherein said means for matching said output of said non-linear oscillator to said natural variability of said physiological function comprises means for multiplying said output of said non-linear oscillator by a scaling factor.

17. A pacemaker as claimed in claim 16 further comprising means for setting said scaling factor as a fraction of said basic pacing rate.

18. A pacemaker as claimed in claim 14 wherein said non-linear oscillator comprises means for modeling a chaotic system.

19. A pacemaker as claimed in claim 14 wherein said non-linear oscillator comprises means for modeling a Lorentz system.

20. A pacemaker as claimed in claim 14 wherein said non-linear oscillator comprises means for modeling a Duffin system.

21. A pacemaker as claimed in claim 14 wherein said non-linear oscillator comprises means for modeling a Rössler system.

22. A pacemaker as claimed in claim 14 wherein said non-linear oscillator comprises means for modeling a Mackey-Glass system.

23. A pacemaker as claimed in claim 14 further comprising means for generating a random value from said basic therapy and wherein said means for combining comprises means for combining said basic therapy, said variability adjustment and said random value to generate said variability-adjusted therapy.

24. A pacemaker as claimed in claim 14 further comprising means for initializing said non-linear oscillator with initial data values.

25. A pacemaker as claimed in claim 14 wherein said non-linear oscillator comprises means for modeling an autonomous chaotic system.

26. A pacemaker as claimed in claim 14 wherein said non-linear oscillator comprises means for modeling a non-linear chaotic system and further comprising means for supplying said means for modeling a non-autonomous chaotic system with an external data feed.

27. A pacemaker as claimed in claim 14 further comprising value buffer means connected between said output of said non-linear oscillator and said means for matching for controlling transfer of signals from said output of said non-linear oscillator to said means for matching.

28. A pacemaker as claimed in claim 27 wherein said value buffer means comprises an N-position memory, controlled by said control means, for reading in and writing out values of said output of said non-linear oscillator, and said control means comprising means for controlling said N-position memory for reading data into said N-position memory at a rate different from reading out said data from said N-position memory.

29. A pacemaker as claimed in claim 14 wherein said non-linear oscillator comprises:

a non-linear oscillator stage which models a chaotic system and which emits a chaotic output; and post-processing means, supplied with said chaotic output for generating an output having a time average of zero.

30. A medical therapy apparatus comprising:

means for administering medical therapy to a subject;

means for modeling a plurality of possible therapy procedures, each therapy procedure having a set of variables associated therewith, for obtaining a plurality of modeled therapy procedure results;

random variable generator means, including a non-linear oscillator, for generating a plurality of random variables for use as said sets of variables; and means for selecting one of said modeled therapy procedure results as optimum for a subject to whom said therapy is to be administered.

* * * * *